United States Patent [19]

Falling et al.

[11] Patent Number: 5,264,595
[45] Date of Patent: Nov. 23, 1993

[54] PROCESS FOR THE PREPARATION OF 3,4-DIHALO-1,2-EPOXYBUTANES FROM 3,4-EPOXY-1-BUTENE

[75] Inventors: Stephen N. Falling; Patricia Lopez-Maldonado, both of Kingsport, Tenn.

[73] Assignee: Eastman Kodak Company, Rochester, N.Y.

[21] Appl. No.: 43,072

[22] Filed: Apr. 5, 1993

[51] Int. Cl.$^5$ .................. C07D 301/00; C07D 303/08
[52] U.S. Cl. ..................................... 549/540; 549/563
[58] Field of Search ........................... 549/540

[56] References Cited

U.S. PATENT DOCUMENTS 4,116,984  9/1978  Prinzbach et al. ............... 549/540
5,103,028  4/1992  Falling et al. ..................... 549/540

OTHER PUBLICATIONS

Shellhamer et al., *J. Heterocyclic Chem.*, 20, pp. 229–232 (1983).
Chemical Abstracts 82:86251k [Movsumzade et al., Dokl. Akad. Nauk. Az. SSR, 30, 14 (1974)].

Primary Examiner—Joseph E. Evans
Attorney, Agent, or Firm—J. Frederick Thomsen; William P. Heath, Jr.

[57] ABSTRACT

Disclosed is a process for the preparation of 3,4-dichloro and 3,4-dibromo-1,2-epoxybutane by the reaction of 3,4-epoxy-1-butene with chlorine or bromine in the presence of a catalytic amount of a tertiary amine or a hydrohalide of a primary, secondary or tertiary amine. The reaction preferably is carried out by the addition of 3,4-epoxy-1-butene and chlorine or bromine to an organic, halogenation solvent containing chlorine or bromine and tertiary amine or amine hydrohalide catalyst.

8 Claims, No Drawings

PROCESS FOR THE PREPARATION OF 3,4-DIHALO-1,2-EPOXYBUTANES FROM 3,4-EPOXY-1-BUTENE

This invention pertains to the preparation of 3,4-dihalo-1,2-epoxybutanes by the reaction of chlorine or bromine with 3,4-epoxy-1-butene. More specifically, this invention pertains to the chlorination or bromination of 3,4-epoxy-1-butene in the presence of an inert solvent and a catalytic amount of an amine or amine hydrohalide.

The literature contains a number of references to the preparation of 3,4-dichloro-1,2-epoxybutane. British Patent 864,880 describes the synthesis of 3,4-dichloro-1,2-epoxybutane by the dehydrochlorination of 1,3,4-trichlorobutan-2-ol. The preparation of 3,4-dichloro-1,2-epoxybutane by the oxidation of 3,4-dichloro-1-butene with peracetic or performic acid is described in British Patent 784,620 and U.S. Pat. No. 3,150,154 and by Hawkins, J. Chem. Soc., 248, (1959). The preparation of 3,4-dichloro-1,2-epoxybutane by the addition of liquid chlorine to undiluted 3,4-epoxy-1-butene at −30° C. is disclosed by Movsumzade et. al., Dokl. Akad. Nauk. Az. SSR, 30, 14 (1974); Chem. Abstr. 82:86251k (1975).

A study of the ionic and free radical halogenation of 3,4-epoxy-1-butene is reported by Shellhamer et. al., J. Heterocyclic Chem., 20, 229 (1983) although the procedures used in this mechanistic study are not practical for the preparation of 3,4-dichloro-1,2-epoxybutane on a commercial scale. For example, Shellhamer et. al. performed their reactions at very low concentrations and allowed the reactions to proceed to only 20 to 50% of completion. Furthermore, the products were purified by gas chromatography and were described as being unstable liquids which turn light yellow after several days.

We chlorinated 3,4-epoxy 1 butene according to a conventional halogenation procedure by adding a slight stoichiometric excess of chlorine to a 12% solution of 3,4-epoxy-1-butene in dichloromethane at −5° C. to 5° C. Although 3,4-dichloro-1,2-epoxybutane was obtained, about 50% of the 3,4-epoxy-1-butene was converted to high boiling, oligomeric compounds. When the crude product was distilled, 3,4-dichloro-1,2-epoxybutane was obtained in a yield of only 6.5%.

We have discovered that stable 3,4-dichloro and 3,4-dibromo-1,2-epoxybutanes may be conveniently prepared in good yields and high purity by the reaction of 3,4-epoxy-1-butene and chlorine or bromine in the presence of a catalytic amount of a tertiary amine or a hydrohalide of a primary, secondary or tertiary amine. The present invention therefore provides a process for the preparation of a compound having the formula

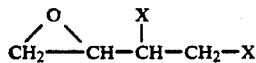

which comprises reacting 3,4-epoxy-1-butene with $X_2$ in the presence of a catalytic amount of a tertiary amine or a hydrohalide of a primary, secondary or tertiary amine wherein X is Cl or Br; and said hydrohalide is HCl or HBr. The process may be carried out in the presence of a conventional halogenation solvent.

The tertiary amine catalysts include trihydrocarbylamines containing a total of 3 to about 60 carbon atoms, preferably about 6 to 18 carbon atoms, and heteroaromatic amines containing a total of 5 to 12 carbon atoms such as unsubstituted and substituted pyridines, quinolines and isoquinolines. As is apparent to those skilled in the art, the particular tertiary amine or amine hydrohalide employed should be stable to chlorine and bromine and exhibit sufficient solubility in the particular halogenation solvent used to effectively catalyze the halogenation reaction. Examples of the tertiary amine catalysts include compounds having the general formulas:

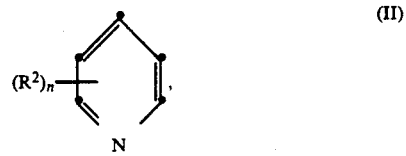

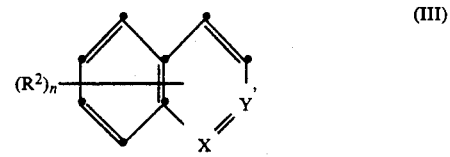

wherein each $R^1$ and $R^2$ individually is a hydrocarbyl group, preferably aliphatic or alicyclic hydrocarbyl group, e.g., alkyl of up to 20 carbon atoms or cycloalkyl such as cyclohexyl, n is 0, 1 or 2, and X and Y are selected from N and CH provided that X and Y are different. Two $R^1$ substituents collectively may represent an alkylene group, e.g., pentamethylene, which with the nitrogen atom to which each is bonded forms a saturated, heterocyclic group, e.g., an N alkylpiperidine. Each $R^1$ preferably is selected from alkyl of 2 to 6 carbon atoms or 2 $R^1$ substituents collectively represent pentamethylene. Each $R^2$ preferably is selected from lower alkyl, e.g., alkyl of up to 4 carbon atoms, especially methyl. Triethylamine, tributylamine and N methylpiperidine are specific examples of trihydrocarbylamine catalysts. Examples of the heteroaromatic amine catalysts include pyridine, isomers of picoline, isomers of lutidine, quinoline, isoquinoline, and alkylpyridine mixtures such as the commercial mixture known as denaturing pyridine.

The amine hydrohalide catalysts may be the hydrochlorides and hydrobromides of primary and secondary amines as well as the hydrochloride and hydrobromide salts of the above described tertiary amines. Examples of such primary and secondary amines are compounds having the general formulas (IV) and (V):

wherein each of $R^3$, $R^4$ and $R^5$ individually is selected from hydrocarbyl groups, preferably aliphatic or alicyclic hydrocarbyl groups, e.g., alkyl of up to 20 carbon atoms or cycloalkyl such as cyclohexyl. $R^4$ and $R^5$ collectively may represent an alkylene group, e.g., pentamethylene, which with the nitrogen atom to which each is bonded forms a saturated, heterocyclic group, e.g., piperidine. $R^3$ preferably is alkyl of 4 to 12 carbon atoms and $R^4$ and $R^5$ preferably are selected from alkyl of 2 to 12 carbon atoms. Hexylamine, dibutylamine and piperidine are specific examples of the amine components of the amine hydrohalide catalysts which may be used in our novel process.

When using one of the preferred halogenation solvents such as a chlorinated hydrocarbon, the catalysts which are particularly preferred are triethylamine hydrohalide and pyridine hydrohalide. These specific catalysts are sufficiently soluble in the preferred halogenation solvents to enable their use in catalytically effective amounts and are sufficiently water soluble to permit their removal by water washing the 3,4-dihalo-1,2-epoxybutane product. However, it may be possible to utilize the 3,4-dihalo-1,2-epoxybutane product without the removal of the catalyst. The halide anion of the amine hydrohalide or pyridine hydrohalide normally is the same as the halogen X used in the process. The catalytically effective amount of the catalyst compound typically is in the range of about 0.001 to 0.1 mole of catalyst per mole of 3,4-epoxy 1-butene.

The organic, halogenation solvent normally used in the process of the present invention may be selected from various aliphatic, cycloaliphatic, aromatic hydrocarbons and halogenated derivatives thereof. Halogenated hydrocarbons, such as chlorinated alkanes and halobenzenes, e.g., dichloromethane, chloroform, carbon tetrachloride, 1,2-dichloroethane, tetrachloroethylene, 1,1,1-triohloroethane, chlorobenzene and the isomers of di and trichlorobenzene, are preferred since the use of non halogenated hydrocarbons may result in product of lower quality and/or halogenation of the solvent. The use of catalyst/solvent combinations comprising (1) triethylamine hydrochloride or bromide with dichloromethane and (2) pyridine hydrochloride or bromide with dichloromethane is particularly preferred.

The halogenation process in general may be carried out at a temperature of about 10° to 70° C. When 3,4-epoxy-1-butene is chlorinated according to our invention, a reaction temperature of about −10° to 20° C. is preferred whereas a range of about 20° to 50° C. is preferred for bromination.

A preferred embodiment of the present invention concerns the addition of 3,4-epoxy-1-butene to a solution of chlorine or bromine and a catalyst in an organic, halogenation solvent. At the commencement of the operation of the process, the halogenation solvent contains dissolved chlorine or bromine. Then chlorine or bromine and 3,4-epoxy-1-butene are added at rates or in increments which maintain dissolved chlorine or bromine in the reaction mixture. At the end of a production run or cycle, the addition of chlorine or bromine is stopped and 3,4-epoxy 1-butene may be added to consume all of the unreacted halogen. Alternatively unreacted halogen may be removed by distillation or by washing with an aqueous inorganic reducing agent (e.g., sodium thiosulfate or sodium bisulfite).

The preferred embodiment described hereinabove comprises a process for the preparation of a compound having the formula

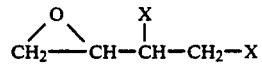

which comprises adding 3,4-epoxy-1-butene and $X_2$ to a solution of $X_2$ and a tertiary amine hydrohalide or pyridine hydrohalide in a chlorinated alkane solvent. The 3,4-epoxy-1-butene and halogen $X_2$ may be added simultaneously or alternately, continuously or intermittently to always maintain dissolved halogen in the reaction during the process time. The presence of dissolved halogen is evident from the color of the reaction mixture: a light green for chlorine and a light orange for bromine. At the conclusion of the process, the mixture is given an aqueous work up to remove catalyst and excess halogen.

The halogenation process of the present invention is further illustrated by the following examples. Gas chromatographic (GC) analyses (reported in area percent) were performed on a Hewlett Packard 5890A gas chromatograph with a 30 meter, DB5, 0.32 mm inside diameter, capillary column with a 0.25 micron film thickness. The temperature program was 35° C. (4.5 minutes), 20° C. per minute to 280° C., hold 5 minutes. The structures of the products obtained were confirmed by nuclear magnetic and mass spectrometry.

EXAMPLE 1

A 500 mL, four neck, round bottom flask was equipped with a gas addition tube, condenser, thermocouple, mechanical stirrer, addition funnel, and a cooling bath. To the flask was added 3.47 g (0.0300 mole) of pyridine hydrochloride and 200 mL of dichloromethane. The solution was cooled to 5° to 5° C. then the chlorine gas addition was begun. After the solution had turned light green, 3,4-epoxy-1-butene and chlorine were added simultaneously over about one hour at −5° to 5° C. Forty milliliters of 3,4-epoxy-1-butene were added dropwise and the chlorine addition was controlled so as to keep the reaction solution green in color. After the 3,4-epoxy-1-butene had been added, the chlorine addition was stopped and more 3,4-epoxy-1-butene was added as needed to decolorize the solution. A total of 48.6 g (0.685 mole) of chlorine and 41.6 g (0.594 mole) of 3,4-epoxy-1-butene was added. The mixture was washed three times with 100 mL of water. The mixture was dried with anhydrous magnesium sulfate, filtered, and the solvent was removed from the filtrate by vacuum rotary evaporation (up to about 35° C. and about 30 torr). The crude, colorless product (97.2 g) was vacuum distilled at 7 torr to give 3,4-dichloro-1,2-epoxybutane at 58°–61° C. The colorless liquid weighed 67.97 g (theory 83.69 g, 81.2%) and had a GC assay of 99.7% (51.6/48.4 mixture of diastereomers).

EXAMPLE 2

A 500 mL, four neck, round bottom flask was equipped with a gas addition tube, condenser, thermocouple, mechanical stirrer, addition funnel, and a cooling bath. To the flask was added 4.13 g (0.0300 mole) of triethylamine hydrochloride and 200 mL of dichloromethane. The solution was cooled to −5° to 5° C. then the chlorine gas addition was begun. After the solution had turned light green, 3,4-epoxy-1-butene and chlorine were added simultaneously over about one hour at −5° to 5° C. Forty milliliters of 3,4-epoxy-1-butene were added dropwise and the chlorine addition was controlled so as to keep the reaction solution green in color. After the 3,4-epoxy-1-butene had been added, the chlorine addition was stopped and more 3,4-epoxy-1-butene was added as needed to decolorize the solution. A total of 38.5 g (0.543 mole) of chlorine and 34.8 g (0.497 mole) of 3,4-epoxy-1-butene was added. The mixture was washed with 100 mL of 0.5% aqueous hydrochloric acid, 100 mL of water, and 100 mL of aqueous sodium bicarbonate (50 mL of saturated aqueous sodium bicarbonate plus 50 mL of water). The mixture was dried With anhydrous magnesium sulfate, filtered, and the solvent was removed from the filtrate by vacuum rotary evaporation (up to about 35° C. and about 30 torr). The crude, colorless product (85.93 g) was vacuum distilled at 7 torr to give 3,4-dichloro-1,2-epoxybutane at 58°-61° C. The colorless liquid weighed 60.6 g (theory 70.0 g, 86.6%) and had a GC assay of 99.6%.

EXAMPLE 3

A 500 mL, four neck, round bottom flask was equipped with a gas addition tube, condenser, thermocouple, mechanical stirrer, addition funnel, and a cooling bath. To the flask was added 5.0 g (0.030 mole) of dibutylamine hydrochloride and 200 mL of dichloromethane. The solution was cooled to −5° to 5° C. and then the chlorine gas addition was begun. After the solution had turned light green, 3,4-epoxy-1-butene and chlorine were added simultaneously over about one hour at −5° to 5° C. Forty milliliters of 3,4-epoxy-1-butene were added dropwise and the chlorine addition was controlled so as to keep the reaction solution green in color. After the 3,4-epoxy-1-butene had been added, the chlorine addition was stopped and more 3,4-epoxy-1-butene was added as needed to decolorize the solution. A total of 41.4 g (0.584 mole) of chlorine and 36.1 g (0.515 mole) of 3,4-epoxy-1-butene was added. The mixture was washed with 100 mL of 0.5% aqueous hydrochloric acid, 100 mL of water, and 100 mL of aqueous sodium bicarbonate (50 mL of saturated aqueous sodium bicarbonate plus 50 mL of water). The mixture was dried with anhydrous magnesium sulfate filtered, and the solvent was removed from the filtrate by vacuum rotary evaporation (up to about 35° C. and about 30 torr). The crude, light-yellow product (97.6 g) was vacuum distilled at 7 torr to give 3,4-dichloro-1,2-epoxybutane at 57°-61° C. The colorless liquid weighted 49.35 g (theory 72.62 g, 68.0%) and had a GC assay of 98.1%.

EXAMPLE 4

A 500-mL, four-neck, round-bottom flask was equipped with a gas addition tube, condenser, thermocouple, mechanical stirrer, addition funnel, and a cooling bath. To the flask was added 3.1 g (0.031 mole) of triethylamine and 200 mL of dichloromethane. The solution was cooled to −5° C. to 5° C. then the chlorine gas addition was begun. After the solution had turned light green, 3,4-epoxy-1-butene and chlorine were added simultaneously over about one hour at −5° to 5° C. Forty milliliters of 3,4-epoxy-1-butene were added dropwise and the chlorine addition was controlled so as to keep the reaction solution green in color. After the 3,4-epoxy-1-butene had been added, the chlorine addition was stopped and more 3,4-epoxy-1-butene was added as needed to decolorize the solution. A total of 44.0 g (0.621 mole) of chlorine and 40.5 g (0.578 mole) of 3,4-epoxy-1-butene was added. The mixture was washed twice with 100 mL of 5% aqueous hydrochloric acid, then once with 100 mL of aqueous sodium bicarbonate (50 mL of saturated aqueous sodium bicarbonate plus 50 mL of water). The mixture was dried with anhydrous magnesium sulfate, filtered, and the solvent was removed from the filtrate by vacuum rotary evaporation (up to about 35° C. and about 30 torr). The crude, yellow product (97.7 g) was vacuum distilled at 7-8 torr to give 3,4-dichloro-1,2-epoxybutane at 57°-62° C. The colorless liquid weighed 52.97 g (theory 81.47 g, 65.0%) and had a GC assay of 97.9%.

EXAMPLE 5

A 500-mL, four-neck, round-bottom flask was equipped with a gas addition tube, condenser, thermocouple, mechanical stirrer, addition funnel, and a cooling bath. To the flask was added 2.8 g of dichloromethane. The solution was cooled to −5° to 5° C. then the chlorine gas addition was begun. After the solution had turned light green, 3,4-epoxy-1-butene and chlorine were added simultaneously over about one hour at −5° to 5° C. Forth milliliters of 3,4-epoxy-1-butene were added dropwise and the chlorine addition was controlled so as to keep the reaction solution green in color. After the 3,4-epoxy-1-butene had been added, the chlorine addition was stopped and more 3,4-epoxy-1-butene was added as needed to decolorize the solution. A total of 39.9 g (0.562 mole) of chlorine and 37.4 g (0.534 mole) of 3,4-epoxy-1-butene was added. The mixture was washed twice with 100 mL of 5% aqueous hydrochloric acid, twice with 100 mL of aqueous sodium bicarbonate (50 mL of saturated aqueous sodium bicarbonate plus 50 mL of water), and 100 mL of water. The mixture was dried with anhydrous magnesium sulfate, filtered, and the solvent was removed from the filtrate by vacuum rotary evaporation (up to about 35° C. and about 30 torr). The crude, yellow product (92.93 g) was vacuum distilled at 7 torr to give 3,4-dichloro-1,2-epoxybutane at 59°-61° C. The colorless liquid weighed 53.51 g (theory 75.24 g, 71.1%) and had a GC assay of 98.9%. COMPARATIVE EXAMPLE 1

To a 500 mL, four neck, round bottom flask equipped with a gas addition tube, condenser, thermometer, mechanical stirrer, and cooling bath was added 200 mL of dichloromethane and 34.8 g (0.497 mole) of 3,4-epoxy-1-butene. The solution was cooled to −5° to 5° C. and then the addition of chlorine gas was begun. Chlorine (41.6 g, 0.587 mole) was added at −5° to 5° C. until the solution turned green. The mixture was washed with 100 mL of 10% aqueous sodium thiosulfate and 100 mL of aqueous sodium bicarbonate (50 mL of saturated aqueous sodium bicarbonate plus 50 mL of water). The mixture was dried with anhydrous magnesium sulfate, filtered, and the solvent was removed from the filtrate by vacuum rotary evaporation (up to about 35° C. and about 30 torr). The crude product was distilled at 7 torr to give a 3,4-dichloro-1,2-epoxybutane product fraction at 50°-64° C. The product weighed 4.57 g (theory 70.0 g, 6.53%) and had a GC assay of 89.1%.

COMPARATIVE EXAMPLE 2

To a 500 mL, four neck, round bottom flask equipped with a gas addition tube, condenser, thermometer, mechanical stirrer, addition funnel, and cooling bath was added 200 mL of dichloromethane. The solution was cooled to −5° to 5° C. and then the chlorine gas addition was begun. After the solution had turned light green, 40 g (0.56 mole) of chlorine and 34.8 g (0.497 mole) of 3,4-epoxy-1-butene were added simultaneously over about 60 minutes at −5° to 5° C. so as to keep the solution green in color. The mixture was washed with 100 mL of 10% aqueous sodium thiosulfate and 100 mL of aqueous sodium bicarbonate (50 mL of saturated aqueous sodium bicarbonate plus 50 mL of water). The mixture was dried with anhydrous magnesium sulfate, filtered, and the solvent was removed from the filtrate by vacuum rotary evaporation (up to about 35° C. and about 30 torr). The crude, colorless product was distilled at 7 torr to give a 3,4-dichloro-1,2-epoxybutane product fraction at 58°-61° C. The colorless liquid weighed 22.3 g (31.9%) and had a GC assay of 98.0%.

The advantages afforded by the process of the present invention are shown in the Table wherein the results obtained in Examples I and 2 and Comparative Examples I and 2 are summarized. In the Table, the "ADDITION MODE" column entries refer to (i) the addition of chlorine to a mixture of 3,4-epoxy-1-butene, catalyst and solvent ("Normal") or (ii) the simultaneous addition of chlorine and 3,4-epoxy-1-butene to a mixture of chlorine, catalyst and solvent ("Inverse"); the "CATALYST" column gives the chlorination catalyst, if any ($Et_3N$=triethyl amine); the "CRUDE ASSAY" column gives the GC area percent, disregarding solvent, of the crude product prior to distillation; and the "DISTILLED YIELD" column gives the percent yield of 3,4-dichloro-1,2-epoxybutane after distillation based on the theoretical amount obtainable from the 3,4-epoxy-1-butene used.

TABLE

| EXAMPLE | ADDITION MODE | CATALYST | CRUDE ASSAY | DISTILLED YIELD |
|---|---|---|---|---|
| 1 | Inverse | Pyridine.HCl | 98.7 | 81.2 |
| 2 | Inverse | $Et_3N.HCl$ | 92.0 | 86.6 |
| C-1 | Normal | None | 50.3 | 6.5 |
| C-2 | Inverse | None | 68.3 | 31.9 |

The invention has been described in detail with particular reference to preferred embodiments thereof, but it will be understood that variations and modifications can be effected within spirit and scope of the invention.

We claim:

1. Process for the preparation of a compound having the formula

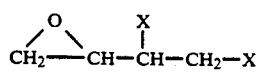

which comprises reacting 3,4-epoxy-1-butene and $X_2$ in the presence of a catalytic amount of a tertiary amine or a hydrohalide of a primary, secondary or tertiary amine wherein X is Cl or Br and said hydrohalide is HCl or HBr.

2. Process according to claim 1 for the preparation of a compound having the formula

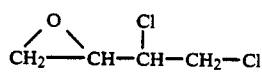

which comprises reacting 3,4-epoxy-1-butene and $Cl_2$ at a temperature of about 10° to 70° C. in the presence of a catalytic amount of a tertiary amine or a hydrohalide of a primary, secondary or tertiary amine wherein the primary, secondary or tertiary amine has the general formula:

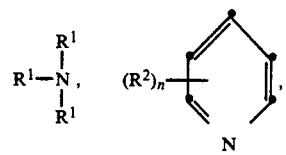

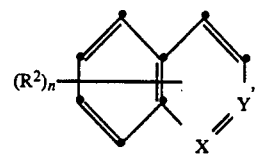

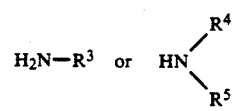

wherein each of $R^1$, $R^2$, $R^3$, $R^4$ and $R^5$ is selected from hydrocarbyl groups, 2 $R^1$ substituents and $R^4$ and $R^5$ collectively represent an alkylene group which with the nitrogen atom to which each is bonded forms a saturated, heterocyclic group, and X and Y are selected from N and CH provided that X and Y are different.

3. Process according to claim 2 wherein the process is carried out at a temperature of about 10° to 20° C. in the presence of a solvent selected from chlorinated hydrocarbons and a catalytic amount of a hydrochloride of a tertiary amine having the general formula:

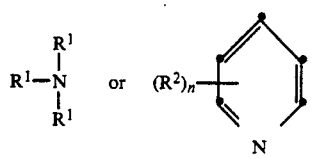

wherein each $R^1$ is selected from alkyl of 2 to 6 carbon atoms, $R^2$ is methyl and n is 0, 1 or 2.

4. Process according to claim 3 wherein the tertiary amine is triethylamine or pyridine and the solvent is dichloromethane.

5. Process for the preparation of a compound having the formula

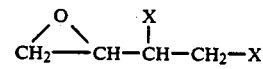

which comprises adding 3,4-epoxy-1-butene and $X_2$ to a solution of $X_2$ and a catalytic amount of a tertiary amine or a hydrohalide of a primary, secondary or tertiary amine wherein X is Cl or Br and said hydrohalide is HCl or HBr.

6. Process for the preparation of a compound having the formula

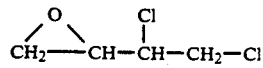

which comprises adding 3,4-epoxy-1-butene and $Cl_2$ to a solution of $Cl_2$ and a catalytic amount of a tertiary amine or a hydrohalide of a primary, secondary or tertiary amine in an organic, halogenation solvent at a temperature of about 10° to 70° C. wherein X is Cl or Br; and said hydrohalide is HCl or HBr.

7. Process according to claim 6 wherein the process is carried out at a temperature of about 10° to 20° C. and in the presence of a solvent selected from chlorinated hydrocarbons and a catalytic amount of a hydrochloride of a tertiary amine having the general formula:

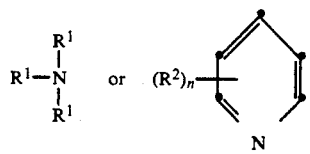

wherein each $R^1$ is selected from alkyl of 2 to 6 carbon atoms, $R^2$ is methyl and n is 0, 1 or 2.

8. Process according to claim 7 wherein the tertiary amine is triethylamine or pyridine and the solvent is dichloromethane.

* * * * *

UNITED STATES PATENT AND TRADEMARK OFFICE
CERTIFICATE OF CORRECTION

PATENT NO. : 5,264,595
DATED : November 23, 1993
INVENTOR(S) : Stephen N. Falling, et al It is certified that error appears in the above-identified patent and that said Letters Patent is hereby corrected as shown below:

Column 7, line 64, (Claim 2), "10°" should be - - -10° - -.

Column 8, line 28, (Claim 3), "10°" should be - - -10° - -.

Column 8, line 67, (Claim 6), "10°" should be - - -10° - -.

Column 9, line 6, (Claim 7), "10°" should be - - -10° - -.

Signed and Sealed this

Twenty-sixth Day of April, 1994

Attest:

BRUCE LEHMAN

*Attesting Officer*   *Commissioner of Patents and Trademarks*